United States Patent
Iordache-Cazana et al.

(10) Patent No.: US 7,384,987 B2
(45) Date of Patent: Jun. 10, 2008

(54) CATALYSTS AND PROCESSES FOR THE MANUFACTURE OF LOWER ALIPHATIC ALCOHOLS FROM SYNGAS

(75) Inventors: Coca Iordache-Cazana, Vancouver (CA); Kevin Smith, Delta (CA)

(73) Assignee: Syntec Biofuel, Inc., Vancouver (CA)

( * ) Notice: Subject to any disclaimer, the term of this patent is extended or adjusted under 35 U.S.C. 154(b) by 230 days.

(21) Appl. No.: 11/138,077

(22) Filed: May 25, 2005

(65) Prior Publication Data

US 2006/0009537 A1 Jan. 12, 2006

Related U.S. Application Data

(60) Provisional application No. 60/575,392, filed on Jun. 1, 2004.

(51) Int. Cl.
C07C 27/00 (2006.01)
(52) U.S. Cl. ............... 518/715; 518/714; 518/717; 518/700
(58) Field of Classification Search ............... 518/700, 518/714, 717
See application file for complete search history.

(56) References Cited

U.S. PATENT DOCUMENTS

| | | |
|---|---|---|
| 4,119,656 A | 10/1978 | Poutsma et al. |
| 4,289,709 A | 9/1981 | Kaiser |
| 4,289,710 A | 9/1981 | Kaiser |
| 4,327,190 A | 4/1982 | Ball et al. |
| 4,440,668 A | 4/1984 | Chang et al. |
| 4,492,772 A | 1/1985 | Ball et al. |
| 4,492,773 A | 1/1985 | Ball et al. |
| 4,552,861 A | 11/1985 | Courty et al. |
| 4,567,160 A | 1/1986 | Nay et al. |
| 4,607,056 A | 8/1986 | Grazioso et al. |
| 4,659,742 A | 4/1987 | Courty et al. |
| 4,749,724 A | 6/1988 | Quarderer et al. |
| 4,752,622 A | 6/1988 | Stevens |
| 4,775,696 A | 10/1988 | Prada-Silva et al. |
| 4,780,481 A | 10/1988 | Courty et al. |
| 4,831,060 A | 5/1989 | Stevens |
| 4,882,360 A | 11/1989 | Stevens |
| 4,943,551 A | 7/1990 | Dombek |
| 4,980,380 A | 12/1990 | Wong et al. |
| 4,983,638 A | 1/1991 | Wong et al. |
| 6,248,796 B1 | 6/2001 | Jackson et al. |

FOREIGN PATENT DOCUMENTS

| | | |
|---|---|---|
| EP | 0100607 | 1/1987 |
| FR | 2523957 | 3/1982 |

OTHER PUBLICATIONS

Japanese abstract (JP 62038337), Saito et al., 1986.*
Chinese abstract (CN 1225852), Luo et al. 1999.*
German abstract (DE 3524317), Roper et al. 1987.*
S. H. Ali, J. G. Goodwin, Jr., SSITKA Investigation of Palladium Precursor and Support Effects on CO Hydrogenation over Supported Pd Catalysts, *Journal of Catalysis* (1998) 176: 3-13.
R. Burch, M. J. Hayes, The Preparation and Characterization of Fe-Promoted $Al_2O_3$-Supported Rh Catalysts for the Selective Production of Ethanol from Syngas, *Journal of Catalysis* (1997) 165: 249-261.
A Gotti, R. Prins, Basic metal oxides as co-catalysts in the conversion of synthesis gas to methanol on supported palladium catalysts, *Journal of Catalysis* (1998) 175: 302-311.
A. F. Gusovius, T.C. Watling, R. Prins, Ca promoted $Pd/SiO_2$ catalysts for the synthesis of methanol from Co: the location of the promoter, *Applied Catalysis A: General* (1999) 188: 187-199.
C. Digane, H. Idriss, J.P. Hindermann, A. Kinnemann, Promoting effects of lithium on $Pd/CeO_2$ Catalysists in carbon monoxide-hydrogen reactions, *Applied Catalysis* (1989) 51: 165-180.
W-Y Kim, T. T. Hanaoka, M. Kishida, K. Wakabayashi, Hydrogenation of carbon monoxide over zirconia supported palladium catalysts using water-oil microemulsion, *Applied Catalysis A: General* (1997) 155:283-289.

* cited by examiner

*Primary Examiner*—J. Parsa
(74) *Attorney, Agent, or Firm*—Price, Heneveld, Cooper, DeWitt & Litton, LLP

(57) ABSTRACT

There are disclosed catalyst formulations and methods for the preparation of oxygenated lower aliphatic compounds. The methods comprise applying a mixture of carbon monoxide and hydrogen to a catalyst formulation under reaction conditions, wherein the catalyst formulation is a solid which may comprise: an active metal, a mixed metal component comprising one or more of a metal A, a metal B, a metal C, and a promoter. In certain embodiments one or more of the metals and the promoter may be present as compounds. In a first embodiment the catalyst comprises a noble metal and an alkali metal promoter, mixed oxides of cerium, zirconium and molybdenum, and an alkali metal promoter. Carbon monoxide and hydrogen may be reacted in the presence of the catalysts disclosed to produce mixtures enriched in lower aliphatic alcohols and particularly ethanol. Various catalyst preparation methods are disclosed including autoignition and gel-sol methods.

30 Claims, No Drawings

CATALYSTS AND PROCESSES FOR THE MANUFACTURE OF LOWER ALIPHATIC ALCOHOLS FROM SYNGAS

FIELD

The present claims and disclosure relate to novel methods to produce ethanol and other lower oxygenated aliphatic compounds from synthesis gas.

BACKGROUND

A number of catalysts are known for the conversion of syngas, a mixture of carbon monoxide, carbon dioxide and hydrogen, to alcohols. For the production of alcohols other than methanol, an obstacle in making the conversion process economically viable is the conversion selectivity of the catalyst. Ethanol is a desirable product for use as a fuel additive but it is not efficiently produced by some of the known catalysts.

A first group of catalysts, the promoted methanol catalysts, usually contain copper oxide or zinc and an alkali metal promoter such as potassium or cesium. These catalysts have high selectivity to methanol and isobutanol and produce very little hydrocarbons. A second class of catalysts include copper and cobalt or other Group VIII metals such as iron. They produce primarily mixtures of methanol, ethanol and propanol, but usually also have high selectivity to hydrocarbons. A third class of catalysts contains molybdenum sulphide as the main component. Selectivity to methanol can be reduced significantly, but again the selectivity for hydrocarbons is high.

SUMMARY

In one aspect there is disclosed a catalyst with improved selectivity to lower oxygenated aliphatics, particularly alcohols and most particularly ethanol.

In particular embodiments the catalyst may be a solid comprising: (a) an active metal selected from the group consisting of Pd, Pt, Rh, Os or Ir; (b) a mixed metal component comprising one or more of: (i) a metal A selected from the group consisting of La, Ce, Sm; and (ii) a metal B selected from the group consisting of Ti, Zr, Hf; and (c) a promoter, the promoter being selected from the group consisting of of Li, Na, K, Rb, Cs and Fr; the gas comprising a mixture of carbon monoxide and hydrogen that react under the reaction conditions in the presence of the catalyst formulation to form an oxygenated lower aliphatic compound.

In a further embodiment the mixed metal component comprises both metal A and metal B.

In a further embodiment the mixed metal component further comprises a metal C selected from the group consisting of Mo, Cr and W.

In a further embodiment, if present: metal A is in the form of a metal A compound; or metal B is in the form of a metal B compound; or metal C is in the form of a metal C compound; or two or more of metals A, B and C are present in the form of compounds.

In a further embodiment the promoter is present in as a promoter compound.

In a further embodiment the metal C is Mo.

In one embodiment there is disclosed a method for the preparation of oxygenated lower aliphatic compounds comprising applying a gas to a catalyst formulation under reaction conditions, wherein the catalyst formulation may be a solid comprising: (a) an active metal selected from the group consisting of Pd, Pt, Rh, Os or Ir; (b) a mixed metal component comprising one or more of: (i) a metal A selected from the group consisting of La, Ce, Sm; and (ii) a metal B selected from the group consisting of Ti, Zr, Hf; and (c) a promoter, the promoter being selected from the group consisting of of Li, Na, K, Rb, Cs and Fr; the gas comprising a mixture of carbon monoxide and hydrogen that react under the reaction conditions in the presence of the catalyst formulation to form an oxygenated lower aliphatic compound.

In a further embodiment the mixed metal component comprises both metal A and metal B.

In a further embodiment the mixed metal component further comprises a metal C selected from the group consisting of Mo, Cr and W.

In a further embodiment, if present: metal A is in the form of a metal A compound; or metal B is in the form of a metal B compound; or metal C is in the form of a metal C compound; or two or more of metals A, B and C are present in the form of compounds.

In a further embodiment the promoter is present in as a promoter compound.

In a further embodiment the metal C is Mo.

In some embodiments there is disclosed a method for the preparation of oxygenated lower aliphatic compounds comprising applying a gas to a catalyst formulation under reaction conditions wherein the catalyst formulation comprises: an active metal wherein the active metal is Pd, Pt, Rh, Os or Ir; a mixed metal wherein the mixed metal component comprises one or more of: (i) a compound of metal A, the metal A being selected from the group consisting of La, Ce, Sm; and (ii) a compound of a metal B, the metal B being selected from the group consisting of Ti, Zr, Hf. The catalyst further comprises a promoter selected from the group consisting of compounds of Li, Na, K, Rb, Cs and Fr. The gas comprises a mixture of carbon monoxide and hydrogen that react under the reaction conditions in the presence of the catalyst formulation to form an oxygenated lower aliphatic compound.

In alternative embodiments the mixed metal component of the catalyst formulation further comprises two or more of: (i) a compound of a metal A, the metal A being selected from the group consisting of La, Ce, Sm; (ii) a compound of a metal B, the metal B being selected from the group consisting of Ti, Zr, Hf; and (ii) a compound of a metal C, the metal C being selected from the group consisting of Mo, Cr and W and the promoter is selected from the group consisting of compounds of Li, Na, K, Rb, Cs and Fr. In alternative embodiments the mixed metal component may include one the compounds of metal A, metal B and metal C.

In further alternative embodiments any one of the compounds of the metal A and metal B is selected from the group consisting of oxides, hydroxides, carbonates and hydroxycarbonates; and the compound of the metal C is selected from the group consisting of oxides, hydroxides, carbonates, hydroxycarbonates, chlorides and fluorides.

In yet further alternative embodiments there is disclosed a method for making a catalyst formulation comprising an active metal, wherein the active metal is Pd, Pt, Rh, Os or Ir; a mixed metal component comprising two or more of: (i) a compound of a metal A, the metal A being selected from the group consisting of La, Ce, and Sm; (ii) a compound of a metal B, the metal B being selected from the group consisting of Ti, Zr, and Hf; and (iii) a compound of a metal C, the metal C being selected from the group consisting of Mo, Cr and W; and a promoter, the promoter being selected from the group consisting of compounds of Li, Na, K, Rb and Cs. The method comprises mixing powdered oxides, carbonates or hydroxycarbonates of two or more of the metal A, the metal B and the metal C; and impregnating the mixture with a solution of a soluble salt of the active metal.

In still further alternative embodiments there is disclosed a method of making a catalyst formulation comprising: an active metal, the active metal being selected from the group consisting of Pd, Pt, Rh, Os and Ir; a mixed metal compound, the mixed metal component comprising two or more components selected from: a compound of a metal A, the metal A being selected from the group consisting of La, Ce, Sm; and a compound of a metal B, the metal B being selected from the group consisting of Ti, Zr, Hf; and a compound of a metal C selected from the group consisting of Mo, Cr and W; a promoter the promoter being selected from the group consisting of compounds of Li, Na, K, Rb and Cs. The method comprises mixing a solution of a soluble salt of at least one of the metal A, the metal B, and the metal C with an alkaline salt of at least one of the others of the metal A, the metal B and the metal C to form a precipitate and impregnating the precipitate with a solution of a soluble salt of the active metal.

In still further alternative embodiments there is disclosed a method of making a catalyst formulation wherein the catalyst formulation comprises: (a) an active metal, the active metal being selected from the group consisting of Pd, Pt, Rh, Os and Ir; (b) a mixed metal component, the mixed metal compound component comprising two or more components selected from: (i) a compound of a metal A, the metal A being selected from the group consisting of La, Ce, Sm (ii) a compound of a metal B, the metal B being selected from the group consisting of Ti, Zr, Hf; and (iii) a compound of a metal B selected from the group consisting of Mo, Cr and W; and a promoter, the promoter being selected from the group consisting of compounds of Li, Na, K, Rb and Cs. The method comprises autoigniting a mixture of salts of metal A and metal B, and impregnating the resulting preparation with suitable forms of the active metal, the metal C and the promoter.

In still further alternative embodiments there is disclosed a method of making a catalyst comprising: (a) an active metal wherein the active metal being selected from the group consisting of Pd, Pt, Rh, Os and Ir; (b) a mixed metal compound, the mixed metal compound comprising two or more components selected from: (i) a compound of a metal A, the metal A being selected from the group consisting of La, Ce, Sm; (ii) a compound of a metal B, the metal B being selected from the group consisting of Ti, Zr, Hf; and (iii) a compound of a metal C selected from the group consisting of Mo, Cr and W; and (c) a promoter, the promoter being selected from the group consisting of compounds of Li, Na, K, Rb and Cs. The method comprises the steps of: (d) mixing solutions of soluble salts of the metal A and the metal B; (e) gelling the mixture with an acid; and (f) impregnating the resulting preparation with the metal C, the active metal and the promoter.

In still further alternative embodiments there is disclosed a method of manufacturing lower aliphatic alcohols from a mixture comprising carbon monoxide and hydrogen, the method comprising reacting the mixture in the presence of the catalyst formulations disclosed.

In still further alternative embodiments there is disclosed a method for the preparation of oxygenated lower aliphatic compounds comprising applying a gas to a catalyst formulation under reaction conditions, wherein the catalyst formulation comprises: (a) an active metal, the active metal being Pd, Pt, or Ir; (b) a mixed metal component, the mixed metal component comprising oxides of Ce, Zr and Mo; and (c) a promoter, the promoter being a compound of Li, Na or K; wherein the applied gas comprises a mixture of carbon monoxide and hydrogen that react under the reaction conditions in the presence of the catalyst formulation to form an oxygenated lower aliphatic compound.

In still further embodiments the lower aliphatic compounds may be alcohols, may be higher alcohols and may be ethanol, propanol or butanol.

In particular embodiments one or more of metal A, B, metal C, and the promoter may each be omitted, and may be present in free form or as compounds.

In a further embodiment there is disclosed a method of making a catalyst formulation comprising: (a) an active metal wherein the active metal is Pd, Pt, Rh, Os or Ir; (b) a mixed metal component wherein the mixed metal component comprises two or more of: (i) a metal A compound, the metal A being selected from the group consisting of La, Ce, and Sm; (ii) a metal B compound, the metal B being selected from the group consisting of Ti, Zr, and Hf; and (iii) a metal C compound, the metal C being selected from the group consisting of Mo, Cr and W; and a promoter compound selected from the group consisting of compounds of Li, Na, K, Rb and Cs; the method comprising: (c) mixing powdered oxides, carbonates or hydroxycarbonates of two or more of the metal A, the metal B and the metal C; and (d) impregnating the mixture with a solution of a soluble salt of the active metal.

In a further embodiment there is disclosed a method of making a catalyst formulation wherein the catalyst formulation comprises: (a) an active metal, the active metal being selected from the group consisting of Pd, Pt, Rh, Os and Ir; (b) a mixed metal component wherein the mixed metal component comprising two or more components selected from: (i) a metal A compound, the metal A being selected from the group consisting of La, Ce, Sm; (ii) a metal B compound, the metal B being selected from the group consisting of Ti, Zr, Hf; and (iii) a metal C compound, the metal C being selected from the group consisting of Mo, Cr and W; and (c) a promoter compound selected from the group consisting of compounds of Li, Na, K, Rb and Cs; the method comprising mixing a solution of a soluble salt of at least one of the metal A, the metal B, and the metal C; with an alkaline salt of at least one of the others of the metal A, the metal B and the metal C to form a precipitate; and impregnating the precipitate with a solution of a soluble salt of the active metal.

There is further disclosed a method of making a catalyst formulation wherein the catalyst formulation comprises: (a) an active metal, the active metal being selected from the group consisting of Pd, Pt, Rh, Os and Ir; (b) a mixed metal component wherein the mixed metal component comprising two or more components selected from: (i) a metal A compound, the metal A being selected from the group consisting of La, Ce, Sm; (ii) a metal B compound, the metal B being selected from the group consisting of Ti, Zr, Hf; and (iii) a metal B compound selected from the group consisting of Mo, Cr and W; and (c) a promoter compound selected from the group consisting of compounds of Li, Na, K, Rb and Cs the method comprising autoigniting a mixture of salts of metal A and metal B, and impregnating the resulting preparation with suitable forms of the active metal, the metal C and the promoter.

There is further disclosed a method of making a catalyst formulation wherein the catalyst formulation comprises: (a) an active metal, the active metal being selected from the group consisting of Pd, Pt, Rh, Os and Ir; (b) a mixed metal compound wherein the mixed metal component comprising two or more components selected from: (i) a metal A compound, the metal A being selected from the group consisting of La, Ce, Sm; (ii) a metal B compound, the metal B being selected from the group consisting of Ti, Zr, Hf; and (iii) a metal C compound selected from the group consisting of Mo, Cr and W and (c) a promoter compound selected from the group consisting of compounds of Li, Na, K, Rb and Cs; the method comprising the steps of: mixing solutions of soluble salts of the metal A and the metal B; gelling the mixture with an acid; and impregnating the resulting preparation with the metal C, the active metal and the promoter.

In further embodiments there is disclosed the catalyst formulation made according to any one of the methods described.

DETAILED DESCRIPTION OF THE PREFERRED EMBODIMENTS

There are disclosed catalyst formulations, methods for their production and methods of their use for the preparation of mixtures comprising oxygenated lower aliphatic compounds starting from gaseous mixtures comprising carbon monoxide and hydrogen. Such mixtures of oxygenated lower aliphatic compounds may for example comprise alcohols and particularly may contain ethanol as a predominant product.

In this application "lower aliphatics", means aliphatic compounds containing one or more carbon atom and includes but is not limited to forms containing 1, 2, 3, 4, 5, 6, 7, 8 or more carbon atoms. Oxygenated lower aliphatics includes but is not limited to acohols, aldehydes, ketones, carboxylic acids and the like.

In this application, "higher alcohols" means alcohols whose molecules contain two or more carbon atoms. It includes ethanol, propanol, butanol, pentanol, hexanol and other alcohols having two or more carbon atoms in their structure.

Composition of the Catalyst Formulation

Catalysts are described that contain an active metal, a mixed metal component and a promoter. The mixed metal component may comprise one or more of two metals, A and B, or may comprise both of metal A and B, or two or more of each of three metals A, B and C. The metals and promoter may be present in free form or as compounds.

In some embodiments the active metal may for example be chosen from the Group VIII metals to the right of and including Ni, Rh and Os in the Periodic Table, such as Pt, Pd and Ir. In specific embodiments, one or more of Pt, Pd and Ir may be used and in particular embodiments Pd may be used.

In some embodiments metal A may be La, Ce or Sm, and Ce is used in selected embodiments. In alternative embodiments metal A may for example be selected from one or more of Pr, Nd, Pm, Sm, Eu, Gd, Tb, Dy, Ho, Er, Tm, Yb, Lu, Th, Pa, U, Np, Py, Am, Cm, Bk, Cf, Es, Fm, Md, No, Lr or any rare earth metal with an atomic number between 57 and 70.

In some embodiments metal B may be selected from the group IV-B elements including but not limited to Ti, Zr, Hf; Rf, and Ce. In particular embodiments the preferred metal B is Ti, Zr and Hf and in some embodiments metal B is Zr. It will be understood that where metal A is Ce, metal B will not be Ce, and vice versa.

In some embodiments metal C may be selected from metals in group VI-B in the periodic table, including but not limited to Cr, Mo, W, Sg Nd and U. In certain embodiments metal B is Cr, Mo or W and in specific embodiments Mo is selected. It has been found that in particular embodiments where the metal C is Mo, it may be desirable to exclude molybdenum sulphides from the composition as their presence may adversely affect the catalyst properties. In some embodiments it may therefore be desirable though not necessarily essential that the free or combined form of metal C be partly, be mostly or exclusively at the surface of the catalyst composition.

The promoter may be selected from free form or compounds of one or more of the alkali metals, including Li, Na, K, Rb, Cs and Fr. Although the some alkaline earth metals may also be useable as promoters, it has been observed that forms or compounds of the alkaline earth metals may promote the production of methanol and decrease ethanol selectivity under some circumstances. In embodiments where alkaline earth metals are not used as a component of the promoter, it may therefore be desirable to exclude them completely or substantially, substantial exclusion being understood to mean that in different embodiments the amount of alkaline earth metal in free compound form will fall below 1.0% of the total catalyst formulation, and in particular embodiments the alkaline earth metal may comprise, for example 0.5% to 1.0%, 0.1% to 0.5%, 0.4% to 0.5%, 0.3% to 0.4%, 0.2% to 0.3%, 0.1% to 0.2%, 0.05% to 0.1%, 0.1% to 0.5%, or 0.0% to 0.1% of the catalyst formulation.

Metals A, B and C and the promoter may be used in combined form, as compounds. A range of alternative compounds may be suitable for use in various embodiments. Possibilities include but are not limited to oxides, hydroxides, nitrides, carbonates, hydroxycarbonates, carbides, phosphides, halides, borides, salicylides, oxyhalides, carboxylates such as acetates, acetyl acetonates, oxalates, carbonyls and the like. Currently the chosen compounds are generally oxides. It will be appreciated that these compounds may be found in the freshly prepared catalyst but that when any preparation of the catalyst is in use or has been exposed to reaction conditions, a range of intermediate forms comprising one or more of carbides, phosphides, oxides and nitrides may be present.

The gas to be applied to the catalyst formulation may be derived from a variety of sources including but not limited to biomass gas, synthesis gas or syngas, landfill gas, stranded gas, natural gas, gas produced by the partial combustion of hydrocarbons, gas produced by gasification of hydrocarbonaceous material, gas produced by steam reforming of liquid or gaseous hydrocarbons or any combination of these. All that is necessary is that the gas contains carbon monoxide and hydrogen. For optimal performance and to prolong the life of the catalyst formulation, the applied gas may be cleared of catalyst inhibitors such as sulphides, halides, nitrogen oxides and sulphur oxides before application to the catalyst.

In some embodiments the molar ratio of the metal component of the promoter to the metal B may for example be any value between 0.01 and 1.5 but and in particular embodiments may fall between 0.1 and 1.0. In certain embodiments the ratio of promoter metal to metal B is between 0.1 and 0.5. Ratios of 0.01-0.1, 0.1-0.2, 0.2-0.3, 0.3-0.4, 0.4-0.5, 0.5-0.6, 0.6-0.7, 0.7-0.8, 0.8-0.9, 0.9-1.0 and above 1.0 are all possible in specific embodiments. It has been found that under some circumstances increased promoter content may improve the selectivity for ethanol.

In some embodiments the catalyst may have a surface area of between approximately 1 $m^2/g$ and 2,000 $m^2/g$ and in some embodiments, below 600 $m^2/g$; in some embodiments the surface area may have a value of between 2 $m^2/g$ and 200 $m^2/g$. Ranges of 1-50 $m^2/g$, 50-100 $m^2/g$, 100-200 $m^2/g$, 200-300 $m^2/g$, 300-400 $m^2/g$, 400-500 $m^2/g$, 500-600 $m^2/g$ 800-900 $m^2/g$, 900-1000 $m^2/g$, or in excess of 1000 $m^2/g$ are all possible in specific embodiments.

In some embodiments the active metal may make up any value or range between 0.01% and 20% of the weight of the catalyst. In some embodiments the active metal makes up between 0.01% and 10% of the catalyst and in specific embodiments the active metal makes up approximately 0.05% of the catalyst. Nonetheless, amounts of below 0.01%, 0.01-05%, 0.05-0.1%, 0.1-0.2%, 0.2-0.5%, 0.5-0.75%, 0.75-1.0%, 1.0-2.0%, 2.0-5%, 5.0-10%, 10%-12.5%, 1.5%-15%, 15%-17.5%, 17.5-20% and above 20% may all be appropriate, desirable or useable under certain circumstances and in certain embodiments. In some embodiments the active metal may be deposited partly, mostly or exclusively at surface of the catalyst formulation.

Although a range of possible values for the reaction parameters are given below, in some embodiments reactions are carried out at a temperature value or range of between 250° C. and 450° C., at a pressure value or range of between 20 and 350 atm, and at a flow rate value or range of between 1,000 and 20,000 $h^{-1}$. The gas may be applied to the catalyst formulation at a range of temperatures including but not limited to temperatures anywhere between 50 and 2000° C. In some embodiments the range is 100-600 C and in one embodiment the temperature range is between 250° C. and 450° C. It will be appreciated that temperatures of less than 50° C., from 50-100° C., 100-150° C., 150-250° C., 250-350° C., 350-450° C., 450 -550° C., 550-650° C., 650-750° C., 750-850° C., 850-950° C., 950-1050° C., 1050-1200° C., 1200-1400° C., 1400-1600° C., 1600-1800° C., 1800-2000° C. or above 2000° C. may be desirable under given conditions and may be used in specific embodiments. However, it is generally understood that under normal circumstances and in certain embodiments, maintaining a temperature of at least 200° C. may avoid the formation of volatile metal carbonyls and the consequent accelerated degradation of the catalyst The gas may be applied to the catalyst formulations under a range of pressure conditions, including a value or range of pressure of between 0.5 atm and 700 atm. Although a pressure anywhere from 20-300 atm is used in some embodiments, pressure ranges of 0.69-14 atm, 14-21 atm, 21-70 atm, 70-140 atm, 140-210 atm, 210-280 atm, 280-350 atm, 350-420 atm, 420-490 atm, 490-560 atm, 560-630 atm, 630-700 atm, or above 700 atm are all possible and may be used in specific embodiments.

In different embodiments, gas may be applied to the catalyst formulation at flow rates of between 100 $h^{-1}$ and 10,000 $h^{-1}$. In some embodiments flow rates of between 1000 $h^{-1}$ and 6000 $h^{-1}$ may be suitable and in specific embodiments flow rates of from 4000-6000 $h^{-1}$ may be used. Nonetheless, flowrates of 100-1,000 $h^{-1}$, 1,000-2,000 $h^{-1}$, 2,000-3,000 $h^{-1}$, 3,000-4,000 $h^{-1}$, 4,000-5,000 $h^{-1}$, 5,000-6,000 $h^{-1}$ 7,000-8,000 $h^{-1}$, 8,000-9,000 $h^{-1}$, 9,000-10,000 $h^{-1}$, 10,000-15,000 $h^{\times 1}$ or greater may all be adopted in particular embodiments, with suitable adjustments to the reaction method. Although a range of flow rates is possible, in some embodiments it has been found that substantially lower flow rates may reduce the ethanol yield from the reaction, as illustrated in the examples presented below.

In different embodiments, the ratio of hydrogen to carbon monoxide in the applied gas varied between 1:2 and 4:1 and in the examples given the ratio was generally 1:1. However, a wide range of ratios may be useable. For instance ratios of below 1:10, from 1:10-1:8, 1:8-1:6, 1:6-1:4, 1:4-1:2, 1:2-1:1, 1:1-2:1, 2:1-3:1, 3:1-4:1, 4:1-5:1, 5:1-6:1, 6:1-7:1, 7:1-8:1, 8:1, 8:1-9:1, and above 9:1 may all be suitable or useable in some embodiments under suitable conditions.

It will be apparent that the different embodiments have different properties, including different lower aliphatic alcohols selectivities, different conversion efficiencies and different hydrocarbon selectivities. Some specific parameter values, choices of metals or metal compound, and combinations of the disclosed components may be undesirable or unsuitable under particular circumstances.

Using the methods and catalysts described herein, the applied gas may be reacted to generate a mixture containing lower oxygenated aliphatic compounds, particularly alcohols and most particularly ethanol. It will be appreciated that cyclic compounds, ketones, aldehydes, carboxylic acids, other alcohols and other types of oxygenated compound may equally be produced. The product mixture may contain a high proportion of alcohols and in particular may contain a high proportion of ethanol in preference to methanol or the other lower aliphatic alcohols that may be produced. In some embodiments the ratio of ethanol to methanol in the product mixture may exceed 7 to 3. In alternative embodiments the product mixture may comprise more than 50%, more than 60%, more than 70%, more than 80% or more than 90% ethanol. Ethanol contents of 10%-30%, 30%-40%, 40%-50%, 50%-60%, 60%-70%, 70%-80%, 80%-90%, or over 90% may be obtainable with different embodiments, depending on the composition of the catalyst formulation, the reaction conditions and the composition of the applied gas.

In certain embodiments and under suitable conditions the values or ranges of the selectivity for the conversion of carbon monoxide to oxygenated lower aliphatic products, and for ethanol in particular, may be 10%-20%, 20%-30%, 30%-40%, 40%-50%, 50%-60%, 60%-70%, 70%-80%, an in particular embodiments may be in excess of 80%. Herein selectivity means the number of carbon atoms appearing in the product in question, divided by the number of carbon monoxide molecules converted to all products other than carbon dioxide. By selectivity for alcohols is meant the total number of carbon atoms appearing in the alcohol or alcohols in question divided by the total carbon atoms appearing in all products (oxgenated or otherwise) other than carbon dioxide.

In particular embodiments the catalyst formulation may be held on a support which support may have a surface area of between 50 and 1000 $m^2/g$ or greater than 1100 $m^2/g$. In some embodiments the support has a surface area of between 100 and 800 $m^2/g$ and in some specific embodiments it has a surface area between 100 and 500 $m^2/g$. A range of surface areas such as 50-200 $m^2/g$, 200-400 $m^2/g$, 400-600 $m^2/g$, 600-800 $m^2/g$, 800-1000 $m^2/g$ or more may all be used, in particular embodiments, though the properties of the particular catalyst preparation may be affected thereby. Possible support materials may include aluminas, basic oxides, silicas, carbon, solid compounds of: magnesium, calcium, strontium, barium, scandium, yttrium, lanthanum, the rare earths, titanium, zirconium, hafnium, vanadium, niobium, tantalum, thorium, uranium and zinc. Oxides are one example of suitable solids but numerous other alternatives may be useable for example: in particular embodiments carbon, ploymers, zeolites, molecular sieves or combinations thereof may be used. The supports are preferably neutral or basic or may be made so by the addition of alkaline promoter. The alumina supports include the alpha, gamma and beta types and the silicas include but are not limited to silica gel, diatomaceous earth, and crystalline silicates. The support may also comprise one or more of the components of the catalyst formulation itself, namely the active metal, the promoter compound and the compounds of metals A, B and C.

In certain embodiments the selectivity for the conversion of carbon monoxide to hydrocarbons may be less than 20%, less than 10%, may be from 5-10%, may be less than 5%, less than 3%, or as low as 1% or less. Particular embodiments may yield ethanol at a rate of 20-40, 40-50, 50-60, 60-80 or more than 80 grams of ethanol per kg of catalyst per hour.

It will be apparent from the examples that follow that under some circumstances one or more of the components of the catalyst composition may be dispensed with and still yield a functional, though possibly sub-optimal, catalyst.

Preparation of the Catalyst Formulation

A number of methods are disclosed for the preparation of the catalyst. In exemplified embodiments, catalysts were all dried, calcinated and reduced, prior to use.

Method 1: In a first embodiment of the methods for catalyst preparation, bulk form compounds of two or more of metal A, metal B and metal C were mixed. These compounds were generally oxides but could be selected from the full range of possible compounds set out herein and the mixing was achieved by either mechanically mixing the powders or by coprecipitation of the mixed oxides from solution. After mixing, a water soluble salt of the active metal was added and the active metal deposited by adjusting the pH to a suitable value. Generally carbonates and hydroxides were used for this purpose but numerous alternatives including but not limited to urea and bicarbonates may be useable in different embodiments. The resulting catalyst formulation was then dried and calcinated by standard methods before the further addition of promoter. The resulting catalyst formulation was then calcinated by standard methods before being reduced. It will be appreciated that this reduction can be carried out using a variety of known methods, including but not limited to: reducing the metal oxide or other reducible form to yield the metal by thermal treatments in hydrogen or diluted hydrogen (which may, in some embodiments, be anywhere from 1-10% $H_2/N_2$). The reduction may be performed in ammonia or carbon monoxide if the reducible form does not react with carbon monoxide to form carbides. with a wide range of such combination of reagents and conditions being usable in alternative embodiments. In certain embodiments the reduction may be accomplished by treating the formulation with hydrogen gas at elevated temperatures, including but not limited to temperature ranges between about 100° C. and 700° C., including temperature ranges of about 200-300° C., about 300-400° C., about 400-500° C. about 500-600° C., about 600-700° C., about 450-550° C. and in particular embodiments the temperature may be about 500° C.

Method 2: In a second embodiment of the methods for catalyst preparation, a solution of salts of metals A and B was prepared and precipitated with a salt of metal C having the general formula $M_a(C_bN_c)_d$. Generally the salts of metals A and B were nitrates and the metal C salt was Ammonium Molybdate, Ammonium Chromate or Ammonium Tungstate, although suitable equivalents may be useable in certain embodiments. The product was filtered, washed and dried. The dried powder mixture was impregnated with a solution of a soluble salt of the active metal, which was then precipitated by adjusting the pH. The resulting solid was impregnated with an alkali comprising the promoter metal and then dried. The product was calcinated and then reduced as indicated above. In some embodiments the method may results in the deposition of the active metal primarily or exclusively at the surface of the catalyst formulation.

Method 3: In a third method embodiment of the methods for catalyst preparation a wet process known as autoignition or combustion was used to produce ultrafine ceria-zirconia powders with narrow size distribution. The process used an intimate blending among two constituents a fuel and an oxidizer. In certain embodiments the fuel may be amino-acids or acid-alcohols, but in alternative embodiments it may be selected from a range of compounds including but not limited to: amino-alcohols. In some embodiments the oxidizer is a nitrate but in alternative embodiments it may be selected from the range of compounds including but not limited to chlorates, perchlorates, peroxides and permanganates). The powder characteristics may be dependent on flame temperature generated during combustion, which itself may be dependent on the nature of the fuel and the fuel-to-oxidant ratio. Oxidizer compounds of metal A and metal B were mixed with a fuel, which in some embodiments was aminoacetic acid/glycine in the required molar ratios in a minimum volume of deionized water to obtain aqueous solutions. These solutions were thermally dehydrated to remove the solvent excess, resulting in a viscous liquid, hereafter termed the "precursor". As soon as the viscous liquid was formed, the temperature was increased to a point at which point the viscous liquid swelled and autoignited. This autoignition resulted in the rapid evolution of a large volume of gases to produce voluminous powders. The powder was then calcinated using normal procedures to remove traces of undecomposed salts. Powder obtained using a fuel deficient precursor may have the highest surface area, and the surface area may decrease as the proportional content of fuel increases. Associated gas evolution from the autoignition results in a highly porous structure of the resulting powder. After being calcinated to remove undecomposed salts, the powder was impregnated with the appropriate quantity of a dissolved salt of metal C, in practice this salt was normally an ammonium salt, but a range of alternatives including at least water or solvent-soluble salts of the metal C, may be used in different embodiments. The resulting mixture is then calcined according to normal procedures to generate the metal C salt required in the catalyst (normally an oxide). The calcined mixture may then be impregnated with a solution of a soluble salts of the active metal, in some embodiments this may be a nitrate but a range of alternatives such as fluorides, chlorides, bromides, oxides, selenides, organo-compounds: for example acetate can be used in particular alternative embodiments. The dried solid can then be impregnated with a solution of promoter, generally in the form of a hydroxide of the promoter metal although other compounds such as carbonate, bicarbonates, fluorides, chlorides, bromides, phosphates, nitrates, formates, acetates may be used in particular embodiments. Following impregnation the formulation can then be calcined using normal procedures to generate a formulation comprising the promoter.

Method 4: A fourth embodiment of the methods for catalyst preparation is a modified sol-gel method in which the gel is produced by dissolving in water in the presence of an organic complexing agent, soluble compounds of the metal or metals. Ultrafine complex oxide of metals A and B was prepared by a modified sol-gel method. Solutions of soluble salts of metals A and B, are prepared in the appropriate metallic ratio. The salts may be prepared separately and then mixed in the appropriate ratio. In some embodiments such salts may be nitrates but in alternative embodiments they may be, without selected from at least the following: metal-alkoxids, flourides, bromides, chlorides, phosphates. A solution of a complexing polyfunctional hydroxy-acid or a suitable equivalent may then be added slowly to the mixture under constant stirring. In particular embodiments the acid used is citric acid, but in alternative embodiments a range of hidroxy-acids is useable for this function, including but not limited to acid-alcohols, polyacids, amino-acids, amino-alcohols. The solution was kept in a water bath or other suitable temperature regulating apparatus at an appropriate temperature until gelation was complete, and then the as-prepared gels were dried according to standard procedures such as the heating of gel for the complete removal of the solvent in air or in inert gas. The gel was then calcined to obtain a solid solution. The solid-solution was then impregnated with a salt of metal C. In some embodiments this was an ammonium salt but alternatives used in different embodiments include but are not limited to: water or solvent-soluble salts of the metal C. The product was calcined according to standard procedures, and the active metal component and promoter component both added as described in Method 3 above.

Method 5: In certain embodiments, some catalysts have been prepared by "incipient wetness" or "dry" impregnation technique of the required metals onto supports such as alumina, silica, zeolites, and molecular sieves. According to this procedure the volume of the solution containing the precursor does not exceed the pore volume of the support. A solution containing a mixture of cerium nitrate and zirconyl nitrate was prepared and used to impregnate silica gel. The impregnated silica gel was dried and calcined for 4 hours at 500° C. and then impregnated with a solution of ammonium heptamolybdate. The solid was dried at 150° C. The resulting Ce/Zr/Mo oxides comprised 40% by weight of the impregnated silica, and filled 10% of the pore volume. This material was impregnated with $Pd(NO_3)$, calcined at 500° C. and promoted with an alkali metal (K or Cs).

Specific examples of the above preparative methods are presented below. It will be noted that many other ways of drying, calcinating and reducing the catalyst formulation are possible. Possible drying methods include but are not limited to heating, heating a solid in an oven at a temperature above 100° C., or rinsing a solid with ethanol to remove the water, or adding a dehydrating agent, such as NaSO4, to an organic liquid to remove the water. Calcination is carried out by driving out water and volatile constituents from a solid by heating. Possible reducing methods include but are not limited to reduction in ammonia or carbon monoxide if the reducible form does not react with carbon monoxide to form carbides.

Reaction Method

In the examples given below, the prepared catalyst formulation was exposed to syngas at elevated temperature and pressure. The hydrogen/carbon monoxide ratio in the input syngas varied from about 1/2 to 4/1. The operating temperature range was between 200 and 350°C and the pressure range between 500 and 3000 psig.

EXAMPLES

The following examples illustrate specific combinations of components and reaction conditions and serve to illustrate, not to limit, the scope of the invention. In each of the following examples, unless otherwise specified, each catalyst composition was tested with a feed gas containing a 1:1 ratio of hydrogen to carbon monoxide Example 1

A first catalyst comprised palladium, zirconium oxide, cerium oxide, and lithium oxide In this example and the other examples that follow, the catalysts were all prepared in a similar manner unless otherwise indicated. The catalyst was prepared by precipitation-deposition. The support was made from a mechanical mixture of the pure metal oxides or by precipitation of them from soluble salts. Oxide samples were prepared by grinding the mixture of pure oxides with a mortar and pestle for 30-40 min. The dried powder mixture was impregnated with a solution of Pd $(NO_3)_2$ in $HNO_3$ or with $IrCl_3$ in water. A solution of $K_2CO_3$ or $NH_4OH$, was slowly added at 70° C. until the pH value of the mixture reached 10. The dispersion was then aged at the same temperature for 1 h. The noble metal hydroxides were precipitated on the surface of support. The resulting solid was dried at room temperature for 24 hours, then calcinated in air at 500° C. for 4-5 hours. After preparation the catalyst was placed in the reactor and pre-treated in two steps. In the first the catalyst was dried in nitrogen flow at 400° C. for 1 hour, and then in the second step, reduced in a low hydrogen flow rate (max. 45 cc/min) for 10 hours. The temperature was held at 500° C.

The catalyst test procedure consisted of temperature-programmed-reduction followed by syngas conversion and product analysis. The conversion was monitored over a period of about 10-12 hours and the product analysis was done using gas chromatography and mass spectrometry. The behaviour of some variants of this catalyst composition are illustrated in Table 1:

TABLE 1

Alkali promoted $Pd-CeO_2-ZrO_2$ versus $Pd-CeO_2$ and $Pd-ZrO_2$ catalysts

| Catalyst | $H_2$/CO | Temp K | Press atm | GHSV $h^{-1}$ | Selectivity, c atom % | | | Yield, g/kg cat/hr | |
|---|---|---|---|---|---|---|---|---|---|
| | | | | | Methanol | $C_{2+}OH$ | Hydrocarbon | $C_{2+}OH$ | Alcohols |
| $Pd-CeO_2-Li_2O$ | 1 | 549 | 51 | 45700 | 90 | 1 | 9 | 1 | 44.7 |
| $Pd-ZrO_2-Li_2O$ | 1 | 551 | 51 | 45700 | 72 | 2 | 26 | 2 | 29.8 |
| $Pd-CeO_2-ZrO_2-Li_2O$ | 1 | 545 | 51 | 45700 | 48 | 10 | 42 | 13 | 38.1 |

In this comparison the increased higher alcohols ($C_{2+}OH$) selectivity shown with the third row of Table 1 was associated with mixing the cerium oxide and zirconium oxide before adding the palladium. The mixed oxide showed a significant increase in the higher alcohols yield compared to the Pd—$CeO_2$ and Pd—$ZrO_2$ catalysts used separately.

Example 2

A promoted $CeO_2$—$ZrO_2$ catalyst was operated over a range of gas feed flowrates. The catalysts were prepared as in Example 1 except that both potassium and lithium were added simultaneously from 1M solutions of LiOH and KOH.

TABLE 2

Alkali promoted Pd—$CeO_2$—$ZrO_2$ operated under different GHSV

| Catalyst | $H_2$/CO | Temp K | Press atm | GHSV $h^{-1}$ | Selectivity, c atom % | | | Yield, g/kg cat/hr | |
|---|---|---|---|---|---|---|---|---|---|
| | | | | | Methanol | $C_{2+}OH$ | Hydrocarbon | $C_{2+}OH$ | Alcohols |
| Pd—$CeO_2$—$ZrO_2$—$K_2O$—$Li_2O$ | 1 | 548 | 68 | 45700 | 27 | 10 | 63 | 12.1 | 39.2 |
| Pd—$CeO_2$—$ZrO_2$—$K_2O$—$Li_2O$ | 1 | 549 | 68 | 15100 | 42 | 18 | 40 | 8.1 | 14.6 |
| Pd—$CeO_2$—$ZrO_2$—$K_2O$—$Li_2O$ | 1 | 549 | 68 | 5700 | 50 | 22 | 38 | 3.2 | 6.7 |

Example 3

In this example the alkali promoted $CeO_2$—$ZrO_2$ catalyst was further promoted by the addition of molybdenum oxide. The Pd/$MoO_x$/$CeO_2$—$ZrO_2$ catalyst was prepared by a deposition-precipitation method. A mixture of $ZrO_2$, $CeO_2$ and $MoO_3$ was dispersed in a solution of Pd($NO_3$)$_2$. Subsequently, a 0.25 M $Na_2CO_3$ solution was slowly added to this solution at 70° C. until the pH reached 10. The dispersion was then aged at the same temperature for 1 hour. The resulting solid was filtered and washed with distilled water, dried for 24 hours at room temperature, and then calcined at 400° C. for 1 hour in air. The product was impregnated with 1M KOH. The molar ratio between Pd and K was 0.4. The calcined catalyst was reduced in two steps: initially a flow of $N_2$(396 cc/min) and $H_2$ (40.8 cc/min) was passed over the catalyst for 1 hour at 400° C. and subsequently pure $H_2$(40.8 cc/min) was passed over the catalyst for 12 hours at 500° C.

The results of using this example of the catalyst are set out in Table 3. As will be seen, adding molybdenum oxide to the Pd—$CeO_2$—$ZrO_2$—K catalyst can result and increased selectivity to higher alcohols. As a result the higher alcohols: methanol ratio in the product may under some circumstances be significantly greater than one.

Example 4

In this example, a Group VIII transition metal to the right of Ni, Rh and Os in the Periodic Table is used as a catalyst for higher alcohols synthesis when dispersed on neutral mixed metal oxides. It was found that Pd can be replaced by other metals including Group VIII metals that adsorb CO non-dissociatively, in this case Ir. In both cases (Ir and Pd) the catalysts had the same composition with a metal loading of 1 wt %.

A new method of preparation for the multimetallic catalyst support was used in this example. A solution of Ce($NO_3$)$_3$6$H_2$O was mixed with a solution of ZrO($NO_3$)$_2$n$H_2$O. The support precursor was precipitated from nitrates solution by adding stepwise ammonium heptamolybdate. The temperature of reaction was 90° C., the pH ranged from 4 to 5.5. The hot product was filtered, washed with distilled water and dried in an oven for 12 hours, at 110° C. The dried powder mixture was impregnated with a diluted solution of Pd($NO_3$)$_2$ in $HNO_3$. A solution of $K_2CO_3$ was slowly added at 70° C. until the pH value of the mixture reached 10. The dispersion was then aged at the same temperature for 1 h. The Pd hydroxide was precipitated on the surface of the support.

The resulting solid was impregnated with 1M KOH solution and then dried at room temperature for 24 hours. The product was calcinated at 600° C. to obtain a crystalline structure of the catalyst.

The results of tests using these catalyst formulations are shown in Table 4. The data show that Ir is a suitable catalyst for selective ethanol synthesis. In this example the Ir is dispersed on the neutral, mixed metal oxides. The higher alcohols yield obtained using Ir catalyst was about 35% greater than that obtained with the Pd catalyst.

TABLE 3

Alkali promoted Pd—$CeO_2$—$ZrO_2$ modified by the addition of molybdenum oxide.

| Catalyst | $H_2$/CO | Temp K | Press Atm | GHSV $h^{-1}$ | Selectivity, c atom % | | | Yield, g/kg cat/hr | |
|---|---|---|---|---|---|---|---|---|---|
| | | | | | Methanol | $C_{2+}OH$ | Hydrocarbon | $C_{2+}OH$ | Alcohols |
| Pd—$CeO_2$—$ZrO_2$—$K_2O$— | 1 | 548 | 68 | 5550 | 62 | 14 | 24 | 5.4 | 10.5 |
| Pd—$MoO_x$—$CeO_2$—$ZrO_2$—$K_2O$ | 1 | 549 | 68 | 5665 | 19 | 60 | 21 | 10 | 19.6 |

TABLE 4

Alkali promoted Pd—MoO$_x$—CeO$_2$—ZrO$_2$ versus Ir—MoO$_x$—CeO$_2$—ZrO$_2$ catalysts

| Catalyst and Composn atomic ratio | H$_2$/CO | Temp K | Press atm | GHSV h$^{-1}$ | Selectivity, C atom % | | | Yield, g/kg cat/hr | |
|---|---|---|---|---|---|---|---|---|---|
| | | | | | Methanol | C$_{2+}$OH | Hydrocarbon | C$_{2+}$OH | Alcohols |
| Pd$_{0.002}$Mo$_{0.7}$Ce$_1$Zr$_1$K$_{0.29}$ | 1 | 548 | 68 | 5480 | 47 | 49 | 4 | 18 | 36 |
| Ir$_{0.002}$Mo$_{0.7}$Ce$_1$Zr$_1$K$_{0.29}$ | 1 | 548 | 68 | 5517 | 29 | 54 | 17 | 24.5 | 40.5 |

Example 5

The catalyst of this example uses Pd dispsersed on a neutral mixed metal oxide comprising of molybdenum and cerium oxides and a transition metal oxide from group IV-B (Ti or Zr). Table 5 shows the results of using the compositions of this example. The data show that when Ti replaces Zr, the higher alcohols selectivity decreases significantly, although the hydrocarbon selectivity increases. The formulation was highly selective for alcohols synthesis, although the ethanol fraction of the total alcohols was relatively low.

TABLE 5

Alkali promoted Pd—MoO$_x$—CeO$_2$—ZrO$_2$ versus Pd—MoO$_x$—CeO$_2$—TiO$_2$ catalysts

| Catalyst and Composn atomic ratio | H$_2$/CO | Temp K | Press Atm | GHSV h$^{-1}$ | Selectivity, C atom % | | | Yield, g/kg cat/hr | |
|---|---|---|---|---|---|---|---|---|---|
| | | | | | Methanol | C$_{2+}$OH | Hydrocarbon | C$_{2+}$OH | Alcohols |
| Pd$_{0.002}$Mo$_{0.7}$Ce$_1$Zr$_1$K$_{0.29}$ | 1 | 548 | 68 | 5480 | 19 | 60 | 21 | 10 | 19.6 |
| Pd$_{0.002}$Mo$_{0.7}$Ce$_1$Ti$_1$K$_{0.29}$ | 1 | 548 | 68 | 5458 | 27 | 7 | 67 | 2 | 8.8 |

Example 6

This example demonstrates the use of Pd dispsersed on a neutral mixed metal oxide comprising of Zr and Ce oxides and a transition metal oxide from group VI-B (Cr,Mo,W). The results of using the compositions of this example are shown in Table 6. The data show that metal oxides chosen from Group VI-B all produce some ethanol, but only the formulations containing Mo have ethanol selectivities greater than methanol while at the same time maintaining low hydrocarbon selectivity.

TABLE 6

Alkali promoted Pd—MoO$_x$—CeO$_2$—ZrO$_2$, Pd—WO$_x$—CeO$_2$—ZrO$_2$ and Pd—CrO$_x$—CeO$_2$—ZrO$_2$ catalysts

| Catalyst and Composn atomic ratio | H$_2$/CO | Temp K | Press atm | GHSV h$^{-1}$ | Selectivity, C atom % | | | Yield, g/kg cat/hr | |
|---|---|---|---|---|---|---|---|---|---|
| | | | | | Methanol | C$_{2+}$OH | Hydrocarbon | C$_{2+}$OH | Alcohols |
| Pd$_{0.002}$Mo$_{0.7}$Ce$_1$Zr$_1$K$_{0.29}$ | 1 | 548 | 68 | 5480 | 19 | 60 | 21 | 10 | 19.6 |
| Pd$_{0.002}$W$_{0.7}$Ce$_1$Zr$_1$K$_{0.29}$ | 1 | 548 | 68 | 5533 | 51 | 9 | 40 | 2 | 5.2 |
| Pd$_{0.002}$Cr$_{0.7}$Ce$_1$Zr$_1$K$_{0.29}$ | 1 | 548 | 68 | 5559 | 29 | 18 | 53 | 5 | 7.3 |

Example 7

This example demonstrates the use of Pd—Mo—Ce—Zr—K catalysts prepared with different Pd loadings. Results are shown in Table 7.

TABLE 7

Alkali promoted Pd—MoO$_x$—CeO$_2$—ZrO$_2$ catalysts with varying Pd content.

| Catalyst and Composn | Pd content | Temp | Press | GHSV | Selectivity, C atom % | | | Yield, g/kg cat/hr | |
|---|---|---|---|---|---|---|---|---|---|
| Atomic ratio | wt % | K | atm | h$^{-1}$ | Methanol | C$_{2+}$OH | Hydrocarbon | C$_{2+}$OH | Alcohols |
| Pd$_{0.002}$Mo$_{0.7}$Ce$_1$Zr$_1$K$_{0.29}$ | 1 | 548 | 68 | 5480 | 19 | 60 | 21 | 10 | 19.6 |
| Pd$_{0.01}$Mo$_{0.7}$Ce$_1$Zr$_1$K$_{0.2}$ | 5 | 548 | 68 | 5906 | 17 | 57.4 | 26.6 | 17 | 26.5 |

The data show that by decreasing the Pd content of the Pd—Mo—Ce—Zr—K catalyst, the higher alcohols selectivity decreases and there is a small decrease in higher alcohols yield.

Example 8

This example compares the results of three different catalyst preparation methods. Pd—Mo—Ce—Zr—K catalyst, prepared by the precipitation-deposition onto a mechanical mixture of metal oxides was compared the same catalyst composition made by an alternative method whereby the three mixed oxides (Mo, Ce and Zr) were first prepared by co-precipitation from solution as described in method 2 above and "dry" impregnation onto silica support as described in method 5. The results of testing these three formulations are shown in Table 8.

TABLE 8

Alkali promoted Pd—MoO$_x$—CeO$_2$—ZrO$_2$ catalysts prepared by three different methods.

| Catalyst and Composn Preparation method | Temp | Press | GHSV | Selectivity, C atom % | | | Yield, g/kg cat/hr | |
|---|---|---|---|---|---|---|---|---|
| Atomic ratio | K | Atm | h$^{-1}$ | Methanol | C$_{2+}$OH | Hydrocarbon | C$_{2+}$OH | Alcohols |
| Pd$_{0.002}$Mo$_{0.7}$Ce$_1$Zr$_1$K$_{0.29}$ Mechanical mixture | 548 | 68 | 5480 | 19 | 60 | 21 | 10 | 19.6 |
| Pd$_{0.002}$Mo$_{0.7}$Ce$_1$Zr$_1$K$_{0.29}$ Precipitation | 548 | 68 | 5412 | 47 | 49 | 4 | 18 | 36 |
| Pd$_{0.002}$Mo$_{0.7}$Ce$_1$Zr$_1$K$_{0.29}$ Dry impregnation on silica | 548 | 68 | 5925 | 23 | 75 | 2 | 22 | 42.3 |

The following further examples illustrate the different methods used for the preparation of the catalyst.

Example 9

The catalyst was prepared by precipitation-deposition. The support was made from a mechanical mixture of the pure metal oxides or by precipitation of them from soluble salts. Multimetallic oxide samples were prepared by grinding the mixture of pure oxides with a mortar and pestle for 30-40 min. The dried powder mixture was impregnated with a solution of Pd (NO$_3$)$_2$ in HNO$_3$ or with IrCl$_3$ in water. A solution of K$_2$CO$_3$ or NH$_4$OH, was slowly added at 70° C. until the pH value of the mixture reached 10. The dispersion was then aged at the same temperature for 1 h. The active metal hydroxides were exclusively precipitated on the surface of support. The resulting solid was dried at room temperature for 24 hours, then calcinated in air at 500° C. for 4-5 hours. After preparation the catalyst was placed in a reactor and pre-treated in two steps: First the catalyst was dried in nitrogen flow at 400° C. for 1 hour, and then reduced in hydrogen at a low flow rate (max. 45 cc/min) for 10 hours. The temperature was held at 500° C.

Example 10

This method of preparation was used for the PdMoCeZrK catalyst. A solution of Ce(NO$_3$)$_3$.6H$_2$O was prepared separately and then mixed with a solution of ZrO(NO$_3$)$_2$.nH$_2$O. The support precursor was precipitated from nitrates solution by adding stepwise ammonium heptamolybdate. The temperature of reaction was 90° C., the pH ranged from 4 to 5.5. The hot product was filtered, washed with distilled water and dried in an oven for 12 hours, at 110° C. The dried powder mixture was impregnated with a solution of Pd (NO$_3$)$_2$ in HNO$_3$. A solution of K$_2$CO$_3$ was slowly added at 70° C. until the pH value of the mixture reached 10. The dispersion was then aged at the same temperature for 1 h. The Pd hydroxide was exclusively precipitated on the surface of support. The resulting solid was impregnated with 1M KOH solution and then dried at room temperature for 24 hours. The product was calcinated at 600° C. to obtain a crystalline structure of the catalyst.

Example 11

This example describes the use of autoignition or combustion to produce ultrafine ceria-zirconia powders with narrow size distribution. The process used an intimate blending among the constituents: the fuel (which may be amino-acids; acids-alcohols etc.) and an oxidizer (such as a nitrate). The powder characteristics were dependant on flame temperature generated during combustion, witch itself is dependent on the nature of the fuel and the fuel-to-oxidant ratio. In this example, cerium nitrate, zirconium nitrate and aminoacetic acid (glycine) were mixed in the required molar ratios in a minimum volume of deionized water to obtain aqueous solutions. These solutions, after thermal dehydration (by heating at 110° C. on a hot plate) to remove the solvent excess, resulted in a viscous liquid, hereafter termed as precursor. As soon as the viscous liquid was formed, the temperature of the hot plate was increased to 200° C. at which point the viscous liquid swelled and autoignited, with the rapid evolution of a large volume of gases to produce voluminous powders. Because the time for which the autoignition exists is rather small (<5 sec.), the powder was calcined at 550° C. for 1 hour to remove traces of undecomposed glycine and nitrates. Note that for glycine-nitrate combustion, a glycine-to-oxidant ratio <0.56 is fuel-deficient and a glycine-to-oxidant ratio >0.56 is a fuel-rich ratio. The ceria-zirconia powder obtained through the fuel deficient precursor may have the highest area, and the areas may decrease as the glycine-to-nitrate ratio increases. The minimum amount of fuel used in the case of the fuel deficient ratio may result in a small reaction enthalpy, and hence, the local temperature of the particles remains low, which may prevent the formation of a dense structure. Associated gas evolution may result in a highly porous structure of the product. The ceria-zirconia powder was impregnated with the appropriate quantity of ammonium heptamolybdate dissolved in water, calcined at 125° C. to obtain $MoO_3$ and then, impregnated with a solution of $Pd(NO_3)_2$ in $HNO_3$. The dried solid was impregnated with KOH and then calcined for 5 hours at 500° C.

Example 12

A modified sol-gel process was used to make Ce—Zr catalysts. Cerium nitrate and zirconium nitrate solutions were prepared separately and then mixed in the appropriate metallic ratio. Citric acid solution was then added slowly to the mixture solution under constant stirring. The solution was kept in a water bath at 60° C. until the gelation was complete, and then the as-prepared gels were dried at 120° C. for 24 hours. The gel was calcined at 500° C. for 4 hours to obtain ceria-zirconia solid solution. The solid was impregnated with ammonium heptamolybdate, and calcined for 2 hours at 125° C., and then impregnated with a solution of $Pd(NO_3)_2$ in $HNO_3$. The dried product was impregnated with KOH and then calcined at 500° C. for 5 hours.

Although the claimed subject matter has been described in detail and through numerous examples, it will be understood that such details are illustrative only and that many variations and modifications can be made without departing from the spirit and scope of the subject matter claimed.

The embodiments of the invention in which an exclusive right or privilege is claimed are defined as follows:

1. A method for the preparation of oxygenated lower aliphatic compounds comprising applying a gas to a catalyst formulation under reaction conditions, wherein the catalyst formulation comprises:
   (a) an active metal, said active metal being Pd, Pt, or Ir;
   (b) a mixed metal component, said mixed metal component comprising compounds of Ce, Zr and Mo, other than a sulfide of Mo; and
   (c) a promoter, said promoter being a compound of Li, Na or K wherein said gas comprises a mixture of carbon monoxide and hydrogen that react under the reaction conditions in the presence of the catalyst formulation to form an oxygenated lower aliphatic compound.

2. The method of claim 1, wherein the molar ratio of said promoter to said Zr is between about 0.1 and 1.0.

3. The method of claim 1, wherein the molar ratio of said promoter to said Zr is between 0.01 and 0.1.

4. The method of claim 1, wherein said active metal is at a concentration of less than about 10% by weight.

5. The method of claim 1, wherein most of said active metal is deposited at the surface of said catalyst formulation.

6. The method of claim 5, wherein substantially all of said active metal is deposited at the surface of said catalyst formulation.

7. The method of claim 1, wherein said catalyst formulation further comprises a support.

8. The method of claim 7, wherein said support has a surface area of between 100 and 500 $m^2/g$.

9. The method of claim 7, wherein said support comprises said mixed metal component.

10. The method of claim 1, wherein said promoter compound is selected from the group consisting of, oxides, hydroxides, carbonates, hydroxycarbonates, chlorides and fluorides.

11. The method of claim 1, wherein:
   (a) any one of said Ce and Zr compounds is selected from the group consisting of oxides, hydroxides, carbonates and hydroxycarbonates; and
   b) said Mo compound is selected from the group consisting of oxides, hydroxides, carbonates, hydroxycarbonates, chlorides and fluorides.

12. The method of claim 1, wherein said Ce, Zr and Mo compounds are oxides.

13. The method of claim 1, wherein the source of said applied gas is selected from the group consisting of biomass gas, synthesis gas, landfill gas, stranded gas and natural gas.

14. The method of claim 1, wherein said oxygenated lower aliphatic compounds comprise ethanol.

15. The method of claim 1, wherein said oxygenated aliphatic compounds comprise ethanol and methanol and the ratio of said ethanol to said methanol is more than about 7 to 3.

16. The method of claim 1, wherein said applied gas is at a temperature between 100° C. and 600° C.

17. The method of claim 1, wherein said applied gas is at a temperature between 250° C. and 450° C.

18. The method of claim 1, wherein said applied gas is at a pressure of 20-300 atm.

19. The method of claim 1, wherein selectivity for conversion of said carbon monoxide to said oxygenated lower aliphatic compound is greater than 50%.

20. The method of claim 1, wherein said carbon monoxide is converted to said oxygenated lower aliphatic compounds with a selectivity greater than 70%.

21. The method of claim 1, wherein said conversion of said carbon monoxide to said lower oxygenated aliphatic compounds generates a yield of greater than 50 g of said oxygenated aliphatic compounds per kilogram of catalyst per hour.

22. The method of claim 1, wherein said gas is passed over said catalyst formulation at a temperature of between about 250° C. and 450° C., at a pressure between 20 and 350 atm and at a flowrate between 1,000 and 20,000 $h^{-1}$.

23. The method according to claim 1, wherein the lower aliphatic compounds are alcohols.

24. The method according to claim 23, wherein one of the lower aliphatic compounds is ethanol, propanol, or butanol.

25. The method according to claim 23, wherein the said one of the lower aliphatic compounds is ethanol.

26. A method for the preparation of oxygenated lower aliphatic compounds comprising applying a gas to a catalyst formulation under reaction conditions, wherein the catalyst formulation comprises:

(a) an active metal, said active metal being Pd, Pt, or Ir;
(b) a mixed component comprising metal compounds, the metals of said metal compounds consisting of Ce, Zr and Mo; and
(c) a promoter, said promoter being a compound of Li, Na or K wherein said gas comprises a mixture of carbon monoxide and hydrogen that react under the reaction conditions in the presence of the catalyst formulation to form an oxygenated lower aliphatic compound.

27. The method of claim 26, wherein said compounds of Ce, Zr and Mo are oxides.

28. The method according to claim 27, wherein the lower aliphatic compounds are alcohols.

29. The method according to claim 28, wherein one of the lower aliphatic compounds is ethanol, propanol, or butanol.

30. The method according to claim 28, wherein the said one of the lower aliphatic compounds is ethanol.

* * * * *